United States Patent [19]
Hötzel

[11] Patent Number: 5,391,284
[45] Date of Patent: Feb. 21, 1995

[54] ARRANGEMENT FOR DETERMINING THE LAMBDA VALUE OF AN AIR/FUEL MIXTURE

[75] Inventor: Gerhard Hötzel, Stuttgart, Germany

[73] Assignee: Robert Bosch GmbH, Stuttgart, Germany

[21] Appl. No.: 198,291

[22] Filed: Feb. 18, 1994

[30] Foreign Application Priority Data

Feb. 18, 1993 [DE] Germany .............. 4304966

[51] Int. Cl.⁶ ........................................... G01N 27/26
[52] U.S. Cl. ................... 204/425; 204/426; 204/427; 204/406; 204/412; 123/672; 123/676; 123/677
[58] Field of Search ............... 204/425, 426, 427, 406, 204/412; 123/672, 676, 677

[56] References Cited

U.S. PATENT DOCUMENTS

| | | | |
|---|---|---|---|
| 4,658,790 | 4/1987 | Kitahara | 204/425 |
| 4,905,652 | 3/1990 | Nakajima et al. | 204/425 |
| 5,236,569 | 8/1993 | Murase et al. | 204/425 |
| 5,338,431 | 8/1994 | Yorita et al. | 204/425 |

OTHER PUBLICATIONS

"Multi-Layered Zirconia Oxygen Sensor for Lean Burn Engine Application" by Shigeo Soejima and Shunzo Mase, SAE Technical Paper Series No. 850378 (1985),* pp. 53 to 59.

*Primary Examiner*—John Niebling
*Assistant Examiner*—Bruce F. Bell
*Attorney, Agent, or Firm*—Walter Ottesen

[57] ABSTRACT

An arrangement determines a voltage which indicates the lambda value of an air/fuel mixture supplied to a combustion engine generating exhaust gas during the operation thereof. The arrangement includes a two-cell oxygen probe mounted in the exhaust gas flow of the engine. The two-cell oxygen probe has an exhaust-gas space for the exhaust gas and an ambient-air space for ambient air. The oxygen probe has a pump cell having two electrodes and a sensing cell having two electrodes. A switchover stage outputs a voltage indicating the electric pump current through the pump cell when a control to the lambda value deviating from one is to be made and outputs that Nernst voltage which is taken off between the electrodes of the sensing cell facing into the ambient air and one of the remaining ones of the electrodes when a control to the lambda value one is to be made. For controlling to the lambda value one, the Nernst voltage supplies a significantly more precise signal than the voltage derived from the pump current.

7 Claims, 2 Drawing Sheets

ARRANGEMENT FOR DETERMINING THE LAMBDA VALUE OF AN AIR/FUEL MIXTURE

FIELD OF THE INVENTION

The invention relates to an arrangement for determining a voltage which shows the lambda value, that is, the air/fuel ratio of the air/fuel mixture supplied to an internal combustion engine.

BACKGROUND OF THE INVENTION

An article by S. Soejima et al entitled "Multi-Layered Zirconium Oxygen Sensor for Lean Burn Engine Application" appears in the SAE paper, no. 850378 (1985), pages 53 to 59 and describes a two-cell oxygen probe having a pump cell and a sensing cell. In this oxygen probe, one of the two electrodes of the pump cell and one of the two electrodes of the sensing cell are mounted in a diffusion gap common to both cells. The diffusion gap communicates with an opening through which gas is exchanged between the space having the exhaust gas to be measured and the diffusion gap. When, for example, lean exhaust gas enters the diffusion gap, this is detected by the sensing cell and such a voltage is applied to the pump cell that this pump pumps oxygen from the diffusion gap (via conduction of $O^{2-}$-ions) until the sensing cell indicates the lambda value 1. If, on the other hand, a rich exhaust gas has entered the diffusion gap, then the sequence described above is reversed. Accordingly, the pump currents have different polarities for the two cases. Zero current flows for a lambda value of one. The measurement of the current zero in order to, for example, control to the lambda value one is, however, disturbed, for example, either by heater leakage currents, capacitive currents, electric motor forces or polarizations.

U.S. Pat. No. 4,658,790 discloses an air/fuel-ratio detecting device and a control system for using the same. The arrangement shown in this patent utilizes a two-cell oxygen probe having a sensing cell and a pump cell to which a pump voltage is applied in such a manner that the sensing cell always shows a constant Nernst voltage corresponding to the lambda value one. This is caused by the pump current or $O^{2-}$-ion current which then flows. From this two-cell oxygen probe, one of two voltages is selectively tapped for evaluation, that is, either the applied pump voltage or a voltage showing the pump current. Both voltages indicate the lambda value. The first voltage is emitted by a switchover stage when it is intended to control to the lambda value one; that is, to a stoichiometric air/fuel mixture. Otherwise, the second-mentioned voltage indicating the pump current is emitted.

In U.S. Pat. No. 4,658,790, the measurement of the pump voltage in the region of the lambda value one is described as being less subjected to disturbances than the measurement of the voltage indicating the pump current. However, no significant improvement can be expected because this pump voltage likewise is influenced by the above-mentioned disturbances.

SUMMARY OF THE INVENTION

It is an object of the invention to provide an arrangement for determining a voltage which shows the lambda value of the air/fuel mixture supplied to the internal combustion engine. With this arrangement, voltages can also be detected which show a lambda value close to one.

The arrangement of the invention is for determining a voltage which indicates the lambda value of an air/fuel mixture supplied to a combustion engine generating exhaust gas during the operation thereof. The arrangement includes: a two-cell oxygen probe mounted in the exhaust gas flow of the engine; the two-cell oxygen probe including a housing structure defining an exhaust-gas space for the exhaust gas and an ambient-air space for ambient air; the housing structure having a pump cell and a sensing cell arranged therein; the cells conjointly defining a diffusion gap therebetween common to both cells and the housing structure defining a pass-through opening between the exhaust-gas space and the diffusion gap for facilitating an exchange of gas therebetween; the pump cell having a first pump-cell electrode facing into the exhaust-gas space and a second pump-cell electrode facing into the diffusion gap; the sensing cell having a first sensing-cell electrode facing into the ambient-air space and a second sensing-cell electrode facing into the diffusion gap; said first sensing-cell electrode and any one of said second sensing-cell electrode, said first pump-cell electrode and said second pump-cell electrode providing a Nernst voltage thereacross; a switchover stage including changeover means switchable between a first position for outputting a first voltage Uip when a control is wanted to a lambda value deviating from a lambda value of one and a second position for outputting a second voltage when a control is wanted to the lambda value one; and, the switchover stage further including circuit means for supplying said Nernst voltage UN as said second voltage to the changeover means.

The arrangement of the invention is characterized in that the Nernst voltage is detected as a voltage for the region around the lambda value one and this Nernst voltage is switched by the switchover stage to its output. This Nernst voltage has a greatly pronounced jump response at the lambda value one as known from the lambda probes operating pursuant to the Nernst principle. For this reason, a precise control to the lambda value one can be provided with this voltage because each small deviation from this value leads to a larger voltage deviation in a jump-like manner. In addition, the above-mentioned disturbances have no influence.

Overall, a two-cell oxygen probe includes four electrodes of which two are for the pump cell and two are for the sensing cell. When the Nernst voltage is detected, at least that electrode of the sensing cell which is exposed to the ambient air must be used for this purpose. This electrode is referred to below as the ambient-air electrode. However, as a second electrode, any one of the three other electrodes can be used. The electrodes facing toward the diffusion gap common to both cells should each show essentially the same effect. This effect can advantageously be utilized to check the operability of the cell in that, alternately, the voltages between the ambient-air electrode and one or the other of the two electrodes (facing toward the diffusion gap) are measured and compared by a comparator unit. These two electrodes are referred to below as the diffusion-gap electrodes. The fourth electrode is exposed to the exhaust gas and is referred to as exhaust-gas electrode below. The comparator unit emits a fault signal when the measured voltages deviate too greatly from each other.

The Nernst voltage can be measured across the ambient-air electrode and one of the above-mentioned three electrodes: the exhaust-gas electrode and the two diffusion-gap electrodes. The electrode selected and the potential relationship between the exhaust-gas electrode and the diffusion-gap electrodes selected (short circuit or specific voltage or floating potential) can be freely selected when the following points are considered.

Exhaust gas having a lambda value one can occur at the exhaust-gas electrode with this exhaust gas, however, containing oxygen and an oxidizable gas. At the above-mentioned electrode, this gas is oxidized by the oxygen with the reaction not being completed; instead, and in accordance with the law of mass action, a specific residual portion of oxygen remains which leads to a specific quantity of $O^{2-}$-ions which, in turn, cause a specific potential difference between the exhaust-gas electrode and the ambient-air electrode. If the reaction at the electrode can run to equilibrium, then precisely the Nernst voltage corresponding to the lambda value one is measured. However, if a great deal of exhaust gas is supplied of the above-mentioned composition, then the equilibrium is not reached so that a false lambda value is measured. This error can be avoided when a measurement can be made in the diffusion gap into which the exhaust gas enters and there reacts at the electrodes until equilibrium. A further advantage of the measurement in the diffusion gap is that the electrodes there are less subjected to disturbances caused by deterioration than the exhaust-gas electrode. In contrast, the measurement with the aid of the last-mentioned electrode reacts very rapidly to changes of the lambda value of the exhaust gas.

A mean potential is formed when the diffusion-gap electrodes are short circuited with the exhaust-gas electrode. This mean potential is somewhat more precise than the potential of the exhaust-gas electrode alone and somewhat faster than the potential of the diffusion-gap electrodes alone. When a measurement is made with respect to the diffusion-gap electrodes and the exhaust-gas electrode is free to float, then the above-mentioned high precision is obtained but ion conduction between the exhaust-gas space and the diffusion gap can still occur which can slightly falsify the measurement. The most precise measurement is obtained when such a voltage is applied to the pump cell which is just equal and opposite to the voltage generated by the oxygen partial pressure difference so that no ion current flows. In this case, a complete equilibrium reaction can take place with the exhaust gas entering from the exhaust-gas space. This equilibrium reaction is not disturbed by any influence.

In the arrangement according to the invention, the Nernst voltage is therefore not used only as a control voltage for the pump current but for measuring operations and controlling operations in the region around the lambda value one even as a measuring voltage which is hardly affected by disturbances. The arrangement can be optimally adapted to different uses and it is possible to provide a function check in that the Nernst voltage between the ambient air electrode and any one of the other electrodes is used.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
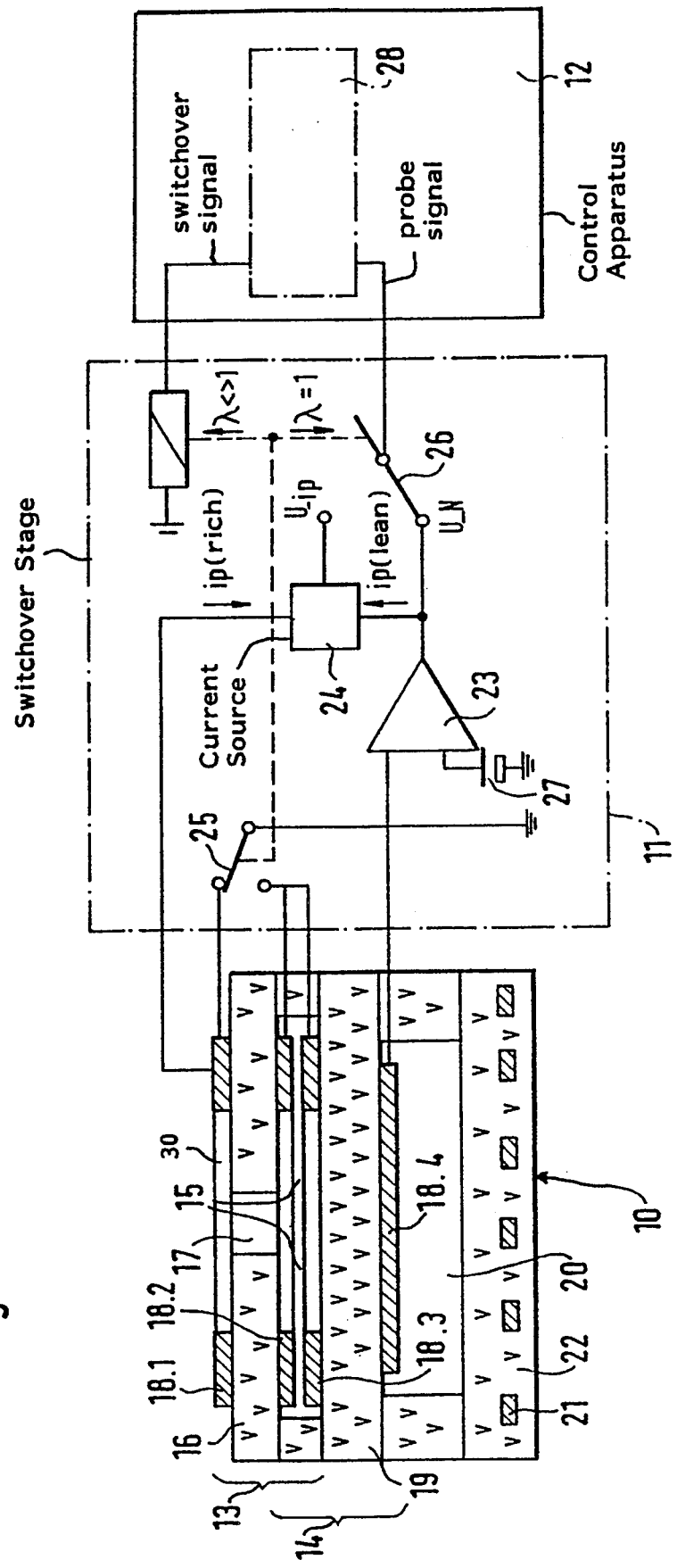
FIG. 1 is a block circuit diagram of a two-cell oxygen probe having a switchover stage for emitting one of two lambda value voltages in dependence upon whether the lambda value is close to one or whether this is not the case.

The arrangement shown in FIG. 1 is for determining a voltage which indicates the lambda value of the air/fuel mixture supplied to an internal combustion engine (not shown). The arrangement comprises a two-cell oxygen probe 10 and a switchover stage 11. The switchover stage 11 supplies its output signal to a control apparatus 12 from which the switchover stage receives a switchover signal. The control apparatus includes a comparator unit 28.

The two-cell oxygen probe 10 comprises an upper pump cell 13 and a lower sensing cell 14. A diffusion gap 15 is common to both cells 13 and 14. The pump cell 13 comprises a zirconium oxide ceramic plate 16 having an exhaust gas pass-through opening 17. The ceramic plate 16 supports a first annular electrode 18.1 on its upper side and a second annular electrode 18.2 on its lower side. The sensing cell 14 comprises a zirconium oxide plate 19 which supports a third annular electrode 18.3 on the upper side thereof and a fourth electrode 18.4 on the lower side thereof. An ambient air space 20 is provided below this fourth electrode. The entire arrangement is heated by a ceramic plate 22 containing heating lines 21.

The switchover stage 11 includes a differential amplifier 23, a current controller 24, an electrode changeover switch 25 as well as a probe-voltage changeover switch 26.

Figure 2:
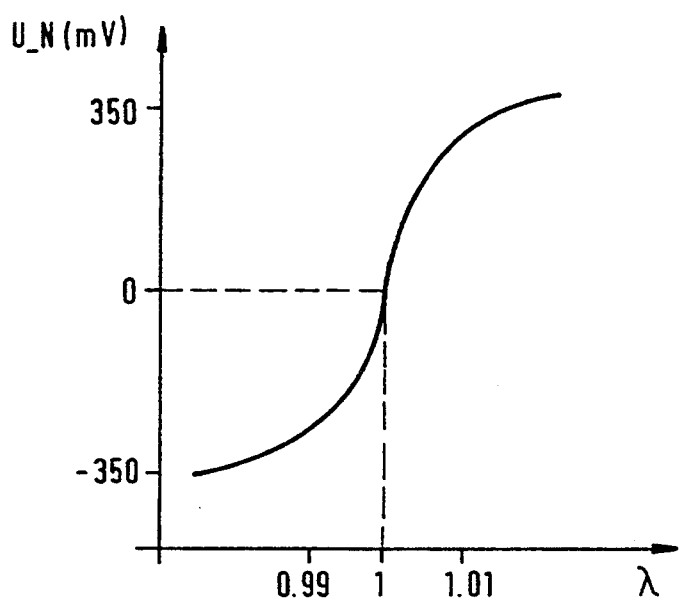
FIG. 2 is a diagram wherein the inverted Nernst voltage of the sensing cell of FIG. 1 is plotted against the lambda value with the Nernst voltage being reduced by a pregiven voltage; and, FIG. 3 is a diagram wherein the pump current of the pump cell of FIG. 1 is plotted against the lambda value.

The operation of the sensing cell 14 will be first explained with respect to FIGS. 1 and 2. First, it is assumed that exhaust gas having the lambda value one is present in the diffusion gap 15. Then, the sensing cell 14 emits a voltage which is typically approximately 450 mV. The voltage of a counter-voltage source 27 is switched in opposition to this voltage of approximately 450 mV in the circuit of FIG. 1 so that the voltage zero is provided at the output of the difference amplifier 23 as shown in FIG. 2 for the lambda value one. The Nernst voltage taken off between the electrodes 18.3 and 18.4 changes considerably with a deviation of the lambda value of the exhaust gas in the diffusion gap 15 of only approximately 1% with this change being approximately 800 mV in the rich range and approximately 100 mV in the lean range. A change from +350 mV to −350 mV occurs because this Nernst voltage is connected counter to the voltage of the counter-voltage source 27. This Nernst voltage is reversed by the differential amplifier 23 so that the trace of FIG. 2 results. This trace extends from approximately −350 mV in the rich range into a region of a few per thousandth about the lambda value one and increases steeply to a voltage of approximately +350 mV in the lean range.

The output voltage of the differential amplifier 23 is applied via the current source 24 to the upper electrode 18.1 of the pump cell 13. As explained above, this output voltage is negative with respect to the lower electrode 18.2 when rich exhaust gas is present in the diffusion gap 15. This negative voltage on the upper electrode 18.1 causes this electrode to press $O^{2-}$-ions through the zirconium oxide plate 16 of the pump cell 13 downwardly to the lower electrode 18.2 where these ions are neutralized to $O_2$ which oxygen is supplied to the diffusion gap 15 and which there leans the rich exhaust gas present until the lambda value one is reached. The differential amplifier 23 then emits the voltage zero which leads to an adjustment of the oxygen pump operation.

If a lean mixture is present in the diffusion gap 15, then the voltage relationships are reversed and, for this reason, the pump operation takes place in the reverse direction; that is, oxygen from the diffusion gap is pumped upwardly into the exhaust gas until the lambda value one adjusts in the diffusion gap. In the first case, it is important that the oxygen can be pumped more rapidly into the diffusion gap than it can again diffuse out therefrom through the exhaust gas entry hole 17 and, in the second case, it is important that oxygen is pumped out of the diffusion gap faster than it is replaced by additional inflowing exhaust gas.

To avoid misunderstanding, it is here noted that in FIG. 1, currents i are shown in the usual manner as flowing from plus to minus; that is, against the electron flow. In the case of a rich mixture, the pump current ip therefore flows away from the upper electrode 18.1. The pump current ip is in each case measured by tapping a voltage Uip which is emitted in the embodiment of FIG. 1 by the current source 24.

Figure 3:
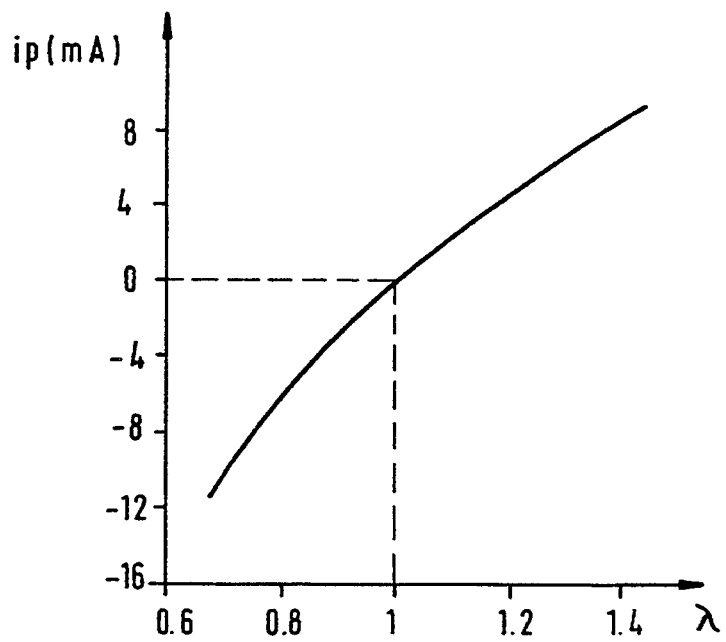

FIG. 3 shows the dependency of the pump current ip on the lambda value. Here it can be seen that this pump current can be measured for both positive and negative values in the lean and rich lambda regions, respectively, with an almost linear trace. A much coarser measurement scale is present for the lambda value around one than in FIG. 2. If the pump current ip is viewed only in a region having a width of a few per thousandth deviation about the lambda value one, then it can be seen that this current does not amount to 0 for all probes for the lambda value one; instead, a scattering is present which corresponds to deviations of several per thousandth of the lambda value. For this reason, a lambda value about one cannot be reliably measured with the aid of the voltage Uip derived from the pump current ip. This, however, is possible without difficulty with the aid of the Nernst voltage UN from the sensing cell 14. The switchover stage 11 emits via the probe voltage changeover switch 26 to the control apparatus 12 either the voltage Uip derived from the pump current for the control to a lambda value unequal to one or the Nernst voltage UN derived from the sensing cell for the control to the lambda value one. The switchover of the probe voltage changeover switch 26 is effected by the above-mentioned switchover signal emitted by the control apparatus 12. If a motor vehicle is driven, for example, in the lower or mid-load range, a lean mixture is preferred so that the control apparatus 12 switches over the probe voltage changeover switch 26 so that the switchover stage 11 emits the voltage Uip. On the other hand, if operating conditions with acceleration or full load are present, then the lambda value should be controlled to one. Then, the control apparatus 12 switches the probe voltage changeover switch 26 so that the switchover stage 11 emits the Nernst voltage UN.

The above-mentioned electrode changeover switch 25 must not necessarily be provided. However, the electrode changeover switch 25 shown in FIG. 1 is advantageous in specific applications. When the Nernst voltage is to be measured, the electrode changeover switch 25 applies the potential from the electrode 18.1 to the differential amplifier 23 in lieu of the potential of the electrode 18.3. In this way, the Nernst voltage across the electrode 18.4 of the sensing cell 14 and the electrode 18.1 of the pump cell 13 is measured. The electrode 18.4 faces toward the ambient air in ambient air space 20 and the electrode 18.1 faces toward the exhaust gas in exhaust-gas space 30 above the plate 16. The last-mentioned electrode 18.1 is subjected directly to the exhaust gas so that changes of the lambda value of the exhaust gas can be immediately determined with the aid of electrode 18.1.

As mentioned above, the Nernst voltage can also be taken off differently which, however, is not shown in the drawings.

The comparator unit 28 shown in FIG. 1 cannot cooperate directly with the switchover stage 11 shown in this figure because the switchover stage 11 detects only a Nernst voltage. However, if the switchover stage 11 is so configured that it performs the function of the changeover explained initially between the two Nernst voltages in the case of the measurement of the exhaust gas about the lambda value one, then the comparator unit 28 operates as described below. First, a switching operation occurs to the Nernst voltage between the ambient-air electrode 18.4 and the lower diffusion-gap electrode 18.3. This first voltage is stored by the comparator unit 28. Then, a switchover to the Nernst voltage of the upper diffusion electrode 18.2 takes place. The second voltage measured thereby is compared to the first measured voltage. If the difference is greater than a pregiven threshold value, then a fault signal is emitted. It is also possible to respectively average several measured first and several second voltages before the comparison is carried out in order to avoid incorrectly outputting a fault signal based on a disturbance occurring by chance.

It should be noted that as a two-cell oxygen probe any desired probe can be used which operates pursuant to the above-described principle, that is, for example, a probe of the kind mentioned in the two publications referred to herein or a probe of this type which is commercially available.

It is understood that the foregoing description is that of the preferred embodiments of the invention and that various changes and modifications may be made thereto without departing from the spirit and scope of the invention as defined in the appended claims.

What is claimed is:

1. An arrangement for determining a voltage which indicates the lambda value of an air/fuel mixture supplied to a combustion engine generating exhaust gas during the operation thereof, the arrangement comprising:

a two-cell oxygen probe mounted in the exhaust gas flow of the engine;

said two-cell oxygen probe including a housing structure defining an exhaust-gas space for said exhaust gas and an ambient-air space for ambient air;

said housing structure having a pump cell and a sensing cell arranged therein;

said cells conjointly defining a diffusion gap therebetween common to both cells and said housing structure defining a pass-through opening between said exhaust-gas space and said diffusion gap for facilitating an exchange of gas therebetween;

said pump cell having a first pump-cell electrode facing into said exhaust-gas space and a second pump-cell electrode facing into said diffusion gap;

said sensing cell having a first sensing-cell electrode facing into said ambient-air space and a second sensing-cell electrode facing into said diffusion gap;

said first sensing-cell electrode and any one of said second sensing-cell electrode, said first pump-cell electrode and said second pump-cell electrode having a Nernst voltage thereacross;

a switchover stage including changeover means switchable between a first position for outputting a first voltage Uip when controlling to a lambda value deviating from a lambda value of one and a second position for outputting a second voltage when controlling to the lambda value one; and, said switchover stage further including circuit means for supplying said Nernst voltage UN as said second voltage to said changeover means.

2. The arrangement of claim 1, said circuit means including means for transmitting said Nernst voltage to said changeover means as a Nernst voltage across said first pump-cell electrode and said first sensing-cell electrode.

3. The arrangement of claim 1, said circuit means including means for transmitting said Nernst voltage to said changeover means as a Nernst voltage across said first sensing-cell electrode and one of said second pump-cell electrode and said second sensing-cell electrode.

4. The arrangement of claim 3, wherein said arrangement is so configured that said first pump-cell electrode is maintained to cause a first pump-cell electrode to be floating with respect to the potential thereon.

5. The arrangement of claim 3, said circuit means including means for causing said first pump-cell electrode to have a potential thereon with respect to said one electrode with respect to which said Nernst voltage is measured so that no ion current flows.

6. The arrangement of claim 3, said circuit including means for transmitting said Nernst voltage to said changeover means alternately as a Nernst voltage across each of the following: said first sensing-cell electrode and said first pump-cell electrode, said first sensing-cell electrode and said second pump-cell electrode, and said first sensing-cell electrode and said second sensing-cell electrode; and, a comparator for comparing the three Nernst voltages to each other and for outputting a fault signal when one of the Nernst voltages deviates from the other Nernst voltages by a set value.

7. The arrangement of claim 1, said circuit means including means for short-circuiting said first pump-cell electrode to one of said second pump-cell electrode and said second sensing-cell electrode and for transmitting said Nernst voltage to said changeover means as a Nernst voltage across said first sensing-cell electrode and said one electrode.

* * * * *

UNITED STATES PATENT AND TRADEMARK OFFICE
CERTIFICATE OF CORRECTION

PATENT NO. : 5,391,284

DATED : February 21, 1995

INVENTOR(S) : Gerhard Hötzel

It is certified that error appears in the above-identified patent and that said Letters Patent is hereby corrected as shown below:

In column 2, line 29:  delete "Uip" and substitute -- U_ip -- therefor.

In column 2, line 34:  delete "UN" and substitute -- U_N -- therefor.

In column 5, line 29:  delete "Uip" and substitute -- U_ip -- therefor.

In column 5, line 45:  delete "Uip" and substitute -- U_ip -- therefor.

In column 5, line 47:  delete "UN" and substitute -- U_N -- therefor.

In column 5, line 50:  delete "Uip" and substitute -- U_ip -- therefor.

In column 5, line 52:  delete "UN" and substitute -- U_N -- therefor.

In column 5, line 60:  delete "Uip" and substitute -- U_ip -- therefor.

In column 5, line 65:  delete "UN" and substitute -- U_N -- therefor.

UNITED STATES PATENT AND TRADEMARK OFFICE
CERTIFICATE OF CORRECTION

PATENT NO. : 5,391,284

DATED : February 21, 1995

INVENTOR(S) : Gerhard Hötzel

It is certified that error appears in the above-identified patent and that said Letters Patent is hereby corrected as shown below:

In column 7, line 14: delete "Uip" and substitute -- $U\_ip$ -- therefor.

In column 7, line 20: delete "UN" and substitute -- $U\_N$ -- therefor.

Signed and Sealed this

Twenty-fifth Day of April, 1995

Attest:

BRUCE LEHMAN

*Attesting Officer*     *Commissioner of Patents and Trademarks*